United States Patent
Bullock et al.

[11] 3,956,303
[45] May 11, 1976

[54] CERTAIN DITHIAZOLYLIDENE UREAS

[76] Inventors: Greg A. Bullock, 2225 Patwynn Road, Wilmington, Del. 19810; Silas S. Sharp, 524 Rothbury Road, Wilmington, Del. 19803

[22] Filed: Aug. 20, 1974

[21] Appl. No.: 499,046

Related U.S. Application Data

[63] Continuation-in-part of Ser. No. 404,795, Oct. 9, 1973, abandoned.

[52] U.S. Cl. .................... 260/306.8 R; 260/268 H; 260/293.68; 424/248; 424/267; 424/270; 260/247.1 M; 424/250
[51] Int. Cl.² ....................................... C07D 285/00
[58] Field of Search ................ 260/306.8 R, 268 H, 260/293.68, 247.1

[56] References Cited
OTHER PUBLICATIONS
Wagner, et al., *Synthetic Organic Chemistry*, N.Y., John Wiley and Sons, 1953, p. 645.

*Primary Examiner*—Richard J. Gallagher

[57] ABSTRACT

Novel compounds of the formula:

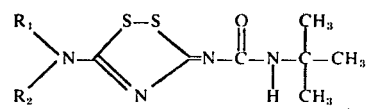

and their use as miticides and mite ovicides, wherein:
$R_1$ is hydrogen, methyl or ethyl;
$R_2$ is methyl, ethyl, methoxy, phenyl, dimethylamino or 2-(dimethylamino)ethyl;
$R_1$ and $R_2$ can be taken together to form

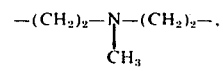

$-(CH_2)_n-$, or $-CH_2CH(CH_3)-O-CH(CH_3)CH_2-$ where $n$ is 4 or 5, provided that, when $R_1$ is hydrogen, $R_2$ must be dimethylamino or 2-(dimethylamino)ethyl.

5 Claims, No Drawings

CERTAIN DITHIAZOLYLIDENE UREAS

RELATED APPLICATIONS

This application is a continuation-in-part of our U.S. Ser. No. 404,795 now abandoned, which was filed Oct. 9, 1973.

BACKGROUND OF THE INVENTION

I. Iwataki, Bull, Chem. Soc. Japan, 45, 3572–79 (1972) described the preparation of two compounds of the formula:

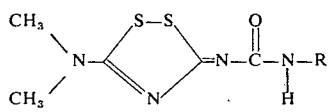

where R is methyl or phenyl. However, no utility is disclosed therein for either of these compounds.

Iwataki et al., Japan Kokai 73 28,470 (Cl. 16E 391), April 14, 1973, (Appln. No. 71 62,565, August 19, 1971) (Chem. Abs., 78, p. 418, Abs. No. 159,610 f) describes 1,2,4-dithiazole derivatives of the formula

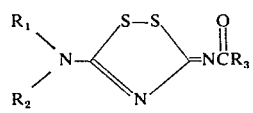

where
$R_1$ and $R_2$ are methyl or phenyl and
$R_3$ is alkyl of 1–19 carbon atoms, phenyl, substituted phenyl, ethoxy, allyl, or trifluoromethyl.
These compounds are disclosed as agricultural insecticides, miticides, and bactericides.

U.S. patent application Ser. No. 358,395, filed May 8, 1973, by Russel F. Bellina, which is a continuation-in-part of U.S. patent application Ser. No. 304,793 now abandoned, filed Nov. 8, 1972, describes a class of compounds of the following two formulas:

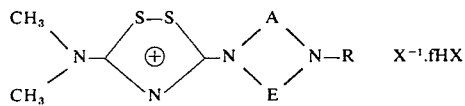

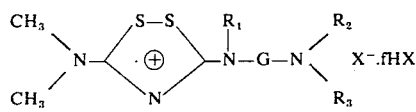

where
R, $R_1$, $R_2$, and $R_3$ are certain organic radicals,
the ring

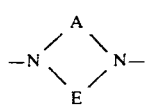

contains 5–8 atoms, and
A, E, and G are alkylene
and the use of these salts as miticides and fungicides.

Each of the compounds disclosed in the three above-mentioned references differ substantially in structure from the compound of the present invention. In addition, none of these references indicate that any of the compounds exhibit any activity as mite ovicides. This is important since a pesticide which is miticidal but not mite ovicidal will relieve the problem only temporarily in the absence of frequent and repeated applications.

SUMMARY OF THE INVENTION

This invention relates to novel miticidal and mite ovicidal compounds of the formula:

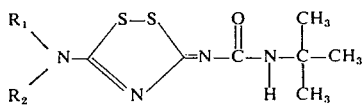

wherein
$R_1$ is hydrogen, methyl or ethyl;
$R_2$ is methyl, ethyl, methoxy, phenyl, dimethylamino or 2-(dimethylamino)ethyl;
$R_1$ and $R_2$ can be taken together to form

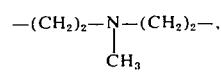

—$(CH_2)_n$—, or —$CH_2CH(CH_3)$—O—$CH(CH_3)CH_2$—, where $n$ is 4 or 5, provided that, when $R_1$ is hydrogen, $R_2$ must be dimethylamino or 2-(dimethylamino)ethyl.

Preferred for their higher degree of insecticidal activity are those compounds of formula I wherein
$R_1$ is methyl or ethyl;
$R_2$ is methyl or ethyl.
Specifically preferred for their very high insecticidal activity are
1-tert-butyl-3-(dimethylamino)-3H-1,2,4-dithiazol-3-ylidene urea and
1-tert-butyl-3-(diethylamino)-3H-1,2,4-dithiazol-3-ylidene urea.

This invention also includes miticidal and mite ovicidal compositions containing at least one of the compounds of the above formula I as active ingredient, a method of controlling mites by applying the compound(s) and/or compositions of the present invention, and a method of preparing the compound(s) of the present invention.

DETAILED DESCRIPTION OF THE INVENTION

Synthesis

The compounds of formula I can be made by either of the following methods:

a. reaction of the hydrochloride salt (or other acid salt) of 3-imino-5-substituted amino-3H-1,2,4-dithiazole with t-butyl isocyanate in an aprotic solvent containing approximately one equivalent of a tertiary amine such as triethylamine or pyridine according to the following reaction scheme:

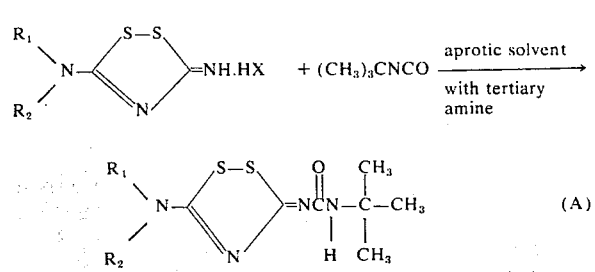

Preferred are those acid salts where X is chlorine, bromine or iodine.

b. reaction of 1-tert-butyl-3(3-thioxo-3H-1,2,4-dithiazol-5-yl)urea with methyl iodide followed by reaction of this product in an aprotic solvent with a substituted amine and a tertiary amine such as triethylamine according to the following reaction scheme:

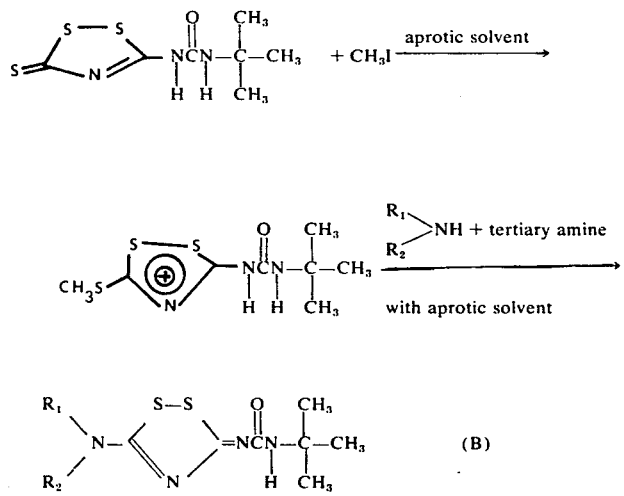

Synthesis of Precursor Dithiazoles

The hydrochloride salt (or other acid salt) of 3-imino-5-substituted-3H-1,2,4-dithiazole described above for method (a) can be prepared by the method described by S. N. Dixit, *J. Indian Chem. Soc.*, 38, 44 (1961), i.e., by reacting the appropriately substituted dithiobiuret with chlorine in an appropriate solvent such as water:

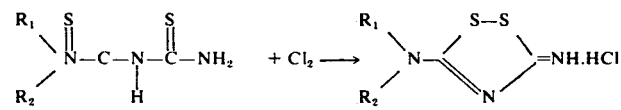

The 1-t-butyl-3(3-thioxo-3H-1,2,4-dithiazol-5-yl)-urea described above for method (b) can be prepared by the method described by R. Seltzer and W. J. Considine, *J. Org. Chem.*, 35, 1665 (1970), i.e., by reacting isoperthiocyanic acid with t-butyl isocyanate in an aprotic solvent such as dioxane:

EXAMPLE 1
PREPARATION OF
1-t-BUTYL-3-(5-DIMETHYLAMINO-3H-1,2,4-DITHIAZOL-3-YLIDENE)UREA

A suspension of 4.75 parts of the hydrobromide salt of 3-imino-5-dimethylamino-3H-1,2,4-dithiazole, two parts of t-butyl isocyanate, two parts of triethylamine, and 50 parts of tetrahydrofuran was stirred and refluxed for two days. The reaction mixture was cooled and the insoluble triethylammonium bromide was removed by filtration and discarded. The filtrate was then evaporated under reduced pressure leaving a white solid, which was recrystallized from isopropanol to afford 3.4 parts of 1-t-butyl-3-(5-dimethylamino-3H-1,2,4-dithiazol-3-ylidene)urea, m.p. 174°–177°C. dec.

NMR (dimethylsulfoxide-$d_6$) : δ ppm 1.3 [S,9H,C(CH$_3$)$_3$], 3.3[S,6H,N(CH$_3$)$_2$]7.42 (broad, 1H,NH).

EXAMPLE 2
PREPARATION OF
N-(1,1-DIMETHYLETHYL)N'-[5-(4-METHYL-1-PIPERAZINYL)-3H-1,2,4-DITHIAZOL-3-YLIDENE]UREA

A suspension of 2.63 parts of 1-t-butyl-3(-3-thioxo-3H-1,2,4-dithiazol-5-yl)urea and 1.42 parts of methyl iodide in 50 parts of tetrahydrofuran was stirred for 1 hour at room temperature and refluxed with stirring for 1 hour. After cooling to room temperature 3.0 parts of triethylamine and 1.0 parts of N-methyl piperazine were added to the suspension and the mixture was stirred at room temperature overnight. The mixture was filtered to remove triethylamine hydroiodide and the solvent was removed from the filtrate under reduced pressure. The filtrate residue was triturated with water and recrystallized from methanol to afford 1.0 part of the title compound, m.p. 169°–172°.

NMR (dimethylsulfoxide-$d_6$) :δ ppm 1.25 [S,9H,C(CH$_3$)$_3$], 2.27 [S,3H, >NCH$_3$]2.48 (broad multiplet, 8H, 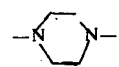

3.8 (broad singlet, >NH.H$_2$O)

The following compounds can be made by appropriate substitution of reactants into the procedure of Example 2.

TABLE 1

$$R_1\text{\textbackslash}N\text{-}\langle\begin{smallmatrix}S\text{-}S\\N\end{smallmatrix}\rangle\text{=NCN-}\overset{O}{\underset{H}{\overset{\|}{C}}}\text{-}\underset{CH_3}{\overset{CH_3}{\overset{|}{C}}}\text{-}CH_3$$

| Example No. | $R_1$ | $R_2$ | °C Melting Point |
|---|---|---|---|
| 3 | Me | Me | 174–177° dec |
| 4 | Et | Me | — |
| 5 | Et | Et | 85–88° |
| 6 | Me | —OMe | — |
| 7 | H | $Me_2N-$ | 147–151° |
| 8 | Me | $Me_2NCH_2CH_2-$ | — |
| 9 | $-(CH_2)_2-\underset{\underset{CH_3}{\|}}{N}-(CH_2)_2-$ | | 169–172° |
| 10 | $-(CH_2)_5-$ | | Oil |

Formulation of the Compound

Useful formulations of the compound of formula I can be prepared in conventional ways. They include dusts, solutions, suspensions, emulsions, wettable powders and granules, emulsifiable concentrates, and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient and at least one of (a) about 0.1% to 20% surfactant(s) and (b) about 1% to 99% solid or liquid diluent(s). More specifically, they will contain these ingredients in the following approximate proportions.

| | Percent by Weight | | |
|---|---|---|---|
| | Active Ingredient | Diluent(s) | Surfactant(s) |
| Wettable Powders and Disposible Granules | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0°C. Polar solvents are required for solution concentrates. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., N.Y. 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules can be made by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for example:

J. B. Buchanan, U.S. Pat. No. 3,576,834 April 27, 1971, Col. 5 Line 36 through Col. 7 Line 70 and Ex. 1–4, 17, 106, 123–140.

R. R. Shaffer, U.S. Pat. No. 3,560,616, Feb. 2, 1971, Col. 3, Line 48 through Col. 7, Line 26 and Examples 3–9, 11–18.

E. Somers, "Formulation", Chapter 6 in Torgeson, "Fungicides", Vol. I, Academic Press, N.Y. 1967.

EXAMPLE 11

Wettable Powder

| | |
|---|---|
| 1-t-butyl-3-(5-dimethylamino-3H-1,2,4-dithiazol-3-ylidene)urea | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

EXAMPLE 12

Aqueous Suspension

| | |
|---|---|
| 1-t-butyl-3-(5-dimethylamino-3H-1,2,4-dithiazol-3-ylidene)urea | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 13

Oil Suspension

| | |
|---|---|
| 1-t-butyl-3-(5-dimethylamino-3H-1,2,4-dithiazol-3-ylidene)urea | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly but preferably after being extended with oils or emulsified in water.

EXAMPLE 14

Dust

| | |
|---|---|
| wettable powder of Example 11 | 10% |
| pyrophyllite (powder) | 90% |

The wettable powder and the pyrophyllite diluent are thoroughly blended and then packaged. The product is suitable for use as a dust. It contains 4% active ingredient.

Uses for the compounds

The compounds of this invention have been found to be useful for control of insects and mites. They are especially useful for control of insects that attack grain and can also be used to protect fruit-bearing trees, nut-bearing trees, ornamental trees, fruit trees, horticultural crops (including ornamentals, small fruit and berries) and grain and seed crops from mites. The compounds are especially suited to protect wheat, corn, barley, rye, oats and sorghum from stored grain pests, and apple, pear, citrus, cherry, plum and peach trees and cotton, peanut and bean plants from mites.

The following is a list of representative pests along with the types of damage that they can cause: *Sitophilus granarius* (granary weevil), which attacks stored grains; *Panonychus ulmi* (European red mite) and *Tetranychus urticae* (two-spotted mite) which are commonly called "orchard mites", and which attack a great many deciduous trees, such as apple, pear, cherry, plum, and peach trees; *Tetranychus atlanticus* (Atlantic or strawberry mite), *T. cinnabarinus* (carmine spider mite) and *T. pacificus* (Pacific mite), which attack cotton and numerous other crop plants; *Paratetranychus citri* (citrus red mite) and others which attack citrus; *Phyllocoptruta oleivora*, which causes citrus rust; *Bryobia praetiosa* (clover mite), which attacks clover, alfalfa, and other crops; and *Aceria neocynodomis*, which attacks grasses and other plants.

Rates of application of the compounds needed to control pests in grain depend on the species involved, extent of infestation, and other factors but are usually in the range of 1–1000 ppm based on the weight of the substrate. One to 100 ppm are preferred and 5–20 ppm are most preferred.

The optimum amount of the compounds needed for mite control depends on a number of variables which are well known to those skilled in the art of plant protection. These include, but are not limited to, the species of mite to be controlled, weather conditions expected, type of crop, stage of development of the crop, and the interval between applications. It may be necessary or desirable to repeat applications within the ranges given one or more times.

Rates of application for the compounds of formula I to crops for mite control are from 0.1 to 4 kilograms of active ingredient per hectare. Rates in the range of 0.2 to 2.0 kg/ha. are preferred. The compound should be applied to ornamental, nut, and fruit trees by spraying to run-off with a solution or suspension containing 25 to 4,000 ppm, preferably about 50 to 1,000 ppm of active ingredient.

The tests described in the folowing example demonstrate the effectiveness of the compositions of the present invention.

For small-scale work the compounds of the invention can be dissolved in acetone and then diluted to spray volume with water containing Surfactant F* at 1-3000.

* A product of NOPCO Chemical Co. comprising polyhydric alcohol esters.

EXAMPLE 15

The foliage of Red Kidney bean plants was infested with adult 2-spotted mites. The plants were then sprayed to run-off with compounds of the invention at a concentration of 150 ppm. The few mites remaining on the treated plants after 48 hours were seriously affected. Seven days after spraying, treated plants were healthy in appearance and free of mites while control plants were heavily damaged by feeding of a heavy mite population.

| Compound | % Kill (48 hrs.) | Live Mites per Leaf (7 Days) |
|---|---|---|
| 1-tert-butyl-3-(5-dimethylamino-3H-1,2,4-dithiazol-3-ylidene)-urea | 94 | 0 |
| 1-tert-butyl-3-(5-diethylamino-3H-1,2,4-dithiazol-3-ylidene)-urea | 96 | 0 |
| 1-tert-butyl-3-[5-(N-ethyl-N-methylamino)-3H-1,2,4-dithiazol-3-ylidene]urea | 93 | 0 |
| 1-tert-butyl-3-[5-(N-methyl-N-phenylamino)-3H-1,2,4-dithiazol-3-ylidene]urea | 96 (600 ppm) | 0 |
| 1-tert-butyl-3-[5-(4-methyl-1-piper- | 95 | 0 |

| Compound | % Kill (48 hrs.) | Live Mites per Leaf (7 Days) |
|---|---|---|
| azinyl)-3H-1,2,4-dithiazol-3-ylidene]urea | | |

EXAMPLE 16

Potted McIntosh apple seedlings were infested with adult female European red mites and the seedlings sprayed to run-off with a solution of 1-tert-butyl-3-(5-dimethyl-3H-1,2,4-dithiazol-3-ylidene)urea at a concentration of 125 ppm. At the end of 5 days, all of the mites on the treated seedlings had died whereas there was no mortality on the untreated control.

EXAMPLE 17

The foliage of Red Kidney bean plants was infested with adult 2-spotted mites. The plants were then sprayed to run-off with the indicated compounds at the listed rates. Forty-eight-hour and seven-day evaluations are set forth in the table below:

| Compound | Spray Concentration (ppm) | % Kill (48 Hrs.) | Live Mites per Leaf (7 Days) |
|---|---|---|---|
| 1-t-butyl-3-(2,2-dimethylhydrazino)-3H-1,2,4-dithiazol-3-ylideneurea | 500 | 99 | 0 |
| 1-t-butyl-3-(1-piperidino)-3H-1,2,4-dithiazol-3-ylideneurea | 600 | 72 | 15 |
| Untreated control | — | 0 | Very heavy infestation |

EXAMPLE 18

A 100-gram sample of wheat seed was treated with an acetone solution of 1-tert-butyl-3-(5-dimethylamino-3H-1,2,4-dithiazol-3-ylidene)urea at rates of 100 and 10 ppm based on weight of the seed and the solvent allowed to evaporate. The wheat was then transferred to glass jars and 100 adult granary weevils were added to each jar. Wheat treated with solvent alone served as the control. The samples of weevil-infested wheat were held in a constant environment room for observation. By the end of 2 weeks all weevils were dead in the jars containing the treated wheat. There was only 2% mortality in the control and the remaining weevils were normal in appearance and feeding on the grain. Similar results were obtained when 1-tert-butyl-3-(5-diethylamino-3H-1,2,4-dithiazol-3-ylidene)urea was used as the treatment.

We claim:
1. A compound of the formula

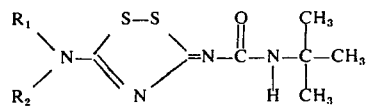

wherein
R$_1$ is hydrogen, methyl or ethyl;
R$_2$ is methyl, ethyl, methoxy, phenyl, dimethylamino or 2-(dimethylamino)ethyl;
R$_1$ and R$_2$ can be taken together to form

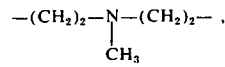

—(CH$_2$)$_n$—, or —CH$_2$CH(CH$_3$)—O—CH(CH$_3$)CH$_2$—, where $n$ is 4 or 5, provided that, when R$_1$ is hydrogen, R$_2$ must be dimethylamino or 2-(dimethylamino)ethyl.

2. The compound of claim 1 wherein R$_1$ is methyl or ethyl and R$_2$ is methyl or ethyl.

3. 1-tert-butyl-3-(dimethylamino)-3H-1,2,4-dithiazol-3-ylidene urea.

4. 1-tert-butyl-3-(diethylamino)-3H-1,2,4-dithiazol-3-ylidene urea.

5. The compound 1-tert-butyl-3-{5-[N-methyl-N-(2-dimethylaminoethyl)amino]-3H-1,2,4-dithiazol-3-ylidene}urea.